US012661429B2

(12) United States Patent
Lee et al.

(10) Patent No.: US 12,661,429 B2
(45) Date of Patent: Jun. 23, 2026

(54) NON-FIXED TYPE IMPLANT FOR CRANIOTOMY AND METHOD OF MANUFACTURING SAME

(71) Applicant: T&R BIOFAB CO., LTD., Siheung-si (KR)

(72) Inventors: Jeong Seok Lee, Seongnam-si (KR); Yun Hyeong Hwang, Seongnam-si (KR); Da Mi Choi, Seongnam-si (KR); Hyun Jung Kim, Seongnam-si (KR); Won Soo Yun, Siheung-si (KR)

(73) Assignee: T&R BIOFAB CO., LTD., Siheung-si (KR)

( * ) Notice: Subject to any disclaimer, the term of this patent is extended or adjusted under 35 U.S.C. 154(b) by 826 days.

(21) Appl. No.: 18/006,379

(22) PCT Filed: Jun. 28, 2021

(86) PCT No.: PCT/KR2021/008115
§ 371 (c)(1),
(2) Date: Jan. 20, 2023

(87) PCT Pub. No.: WO2022/030759
PCT Pub. Date: Feb. 10, 2022

(65) Prior Publication Data

US 2023/0263935 A1 Aug. 24, 2023

(30) Foreign Application Priority Data

Aug. 3, 2020 (KR) ........................ 10-2020-0097049

(51) Int. Cl.
*A61L 27/12* (2006.01)

(52) U.S. Cl.
CPC ..... *A61L 27/12* (2013.01); *A61F 2310/00293* (2013.01); *A61L 2430/02* (2013.01)

(58) Field of Classification Search
CPC ........................... A61F 2/2875; A61F 2/30736
See application file for complete search history.

(56) References Cited

U.S. PATENT DOCUMENTS 5,545,226 A 8/1996 Wingo et al.
6,197,037 B1 * 3/2001 Hair .................... A61B 17/688 606/151

(Continued)

FOREIGN PATENT DOCUMENTS

CN 101360461 A 2/2009
CN 108135700 A 6/2018

(Continued)

OTHER PUBLICATIONS

International Search Report issued in PCT/KR2021/008115; mailed Oct. 5, 2021.

(Continued)

*Primary Examiner* — Alvin J Stewart
(74) *Attorney, Agent, or Firm* — Studebaker Brackett PLLC

(57) ABSTRACT

Proposed is a non-fixing implant made of a raw material including a biomaterial and a ceramic-based composite material having excellent osteoconductivity in addition to a polymer. The non-fixing implant can be accurately secured to a gap between the skull and the bone flap and can be conveniently used. Further proposed is a method of manufacturing the non-fixing implant. The non-fixing implant includes a flexible wedge deformable to conform to the external contour of the bone flap and a plurality of wings connected to an upper or lower portion of the flexible wedge and extending to both sides of the flexible wedge. The wings have a porous structure. The wings on one side will be positioned on the bone flap and the wings on the other side will positioned on the skull. The non-fixing implant has the advantage of being capable of accurately filling a defect (Continued)

(a)

(b)

formed by craniotomy, has improved biocompatibility and bone bonding ability, and allows tissue invasion.

15 Claims, 5 Drawing Sheets

(56) References Cited

U.S. PATENT DOCUMENTS

| | | | | |
|---|---|---|---|---|
| 7,833,253 | B2 * | 11/2010 | Ralph | A61B 17/688 433/172 |
| 2006/0015184 | A1 | 1/2006 | Winterbottom et al. | |
| 2007/0083268 | A1 * | 4/2007 | Teoh | A61L 31/146 623/23.63 |
| 2010/0036413 | A1 | 2/2010 | Nakaji | |
| 2010/0094428 | A1 * | 4/2010 | Ralph | A61B 17/688 606/280 |
| 2012/0283840 | A1 * | 11/2012 | Frederick | A61F 2/4657 623/22.32 |
| 2014/0172116 | A1 * | 6/2014 | Maxson | A61F 2/28 623/23.53 |
| 2018/0200064 | A1 * | 7/2018 | Vallittu | A61F 2/2875 |
| 2021/0000602 | A1 * | 1/2021 | Kumta | B33Y 10/00 |
| 2021/0186702 | A1 * | 6/2021 | Sariibrahimoglu | A61L 31/148 |
| 2022/0202574 | A1 * | 6/2022 | Kuhn | A61L 31/086 |
| 2022/0324170 | A1 * | 10/2022 | Reith | A61F 2/30734 |
| 2023/0277321 | A1 * | 9/2023 | Link | A61F 2/34 623/23.5 |
| 2024/0156602 | A1 * | 5/2024 | Noble | A61F 2/2875 |
| 2024/0277487 | A1 * | 8/2024 | Clemens | A61F 2/30771 |
| 2024/0423804 | A1 * | 12/2024 | Robinson | A61F 2/3094 |
| 2025/0032261 | A1 * | 1/2025 | Goldstein | A61F 2/2875 |

FOREIGN PATENT DOCUMENTS

| | | | | |
|---|---|---|---|---|
| EP | 4574098 | A2 * | 6/2025 | A61F 2/4455 |
| JP | 2007-512083 | A | 5/2007 | |
| KR | 10-1269127 | B1 | 5/2013 | |
| KR | 10-2016-0094803 | A | 8/2016 | |
| KR | 10-2018-0128227 | A | 12/2018 | |
| KR | 10-2115529 | B1 | 5/2020 | |
| WO | WO-2016024248 | A1 * | 2/2016 | A61F 2/30965 |
| WO | 2017/210688 | A1 | 12/2017 | |
| WO | 2020/028268 | A1 | 2/2020 | |
| WO | WO-2023215156 | A1 * | 11/2023 | A61B 17/68 |
| WO | WO-2025163577 | A1 * | 8/2025 | A61F 2/2875 |

OTHER PUBLICATIONS

Matrix Surgical USA; Omnipore® Surgical Implant Catalog; Feb. 5, 2020, Total 20 pages.

Zhang, L. et al; "Three-dimensional (3D) printed scaffold and material selection for bone repair"; Acta Biomaterialia; 2019; pp. 16-33; vol. 84.

Decision to Grant a Patent; mailed by the Japanese Patent Office on Oct. 31, 2023, which corresponds to Japanese Patent Application No. 2023-506179 and is related to U.S. Appl. No. 18/006,379.

The extended European search report issued by the European Patent Office on Dec. 4, 2023, which corresponds to European Patent Application 21853001.2-1122 and is related to U.S. Appl. No. 18/006,379.

Office Action issued in CN 202180057684.7; mailed by the China National Intellectual Property Administration on Mar. 22, 2025.

* cited by examiner (a)

(b)

(a)

(b)

NON-FIXED TYPE IMPLANT FOR CRANIOTOMY AND METHOD OF MANUFACTURING SAME

CROSS-REFERENCE TO RELATED APPLICATIONS

This application is a U.S. National Phase Entry of International Application No. PCT/KR2021/008115 filed on Jun. 28, 2021, which claims the benefit of priority to Korean Patent Application No. 10-2020-0097049 filed on Aug. 3, 2020, the entire content of which is incorporated herein by reference.

TECHNICAL FIELD

The present invention relates to an implant for filling a gap between the skull and the bone flap, created by craniotomy. More particularly, the present invention includes an 3D-printed implant made of a polymer alone or a composite material of a polymer and a ceramic compound having excellent osteoconductivity similar to that of natural bones, and a method of manufacturing the same.

A non-fixing implant for craniotomy, according to the present invention, is manufactured through 3D printing technology to have structural flexibility, can be applied to a site where a defect occurs, and can be accurately bound to a defect due to a wedge-shaped insert thereof. Therefore, the non-fixing implant according to the present invention has the advantage of not requiring an additional fixing device for fixing the implant.

Project Unique Number: P0008811

Government Department: Ministry of Trade, Industry and Energy

Specialized Institution for Project Management: Korea Institute for Advancement of Technology Title of Research Business: Industrial Technology Demonstration Project for 3D Printing Medical Device Title of Research Business: Demonstration of Customized 3D Printing Implant for Surgery Using Polymer-based Biodegradable Material Contribution Rate: 1/1

Research Institute: TNR Biofab Co., Ltd.

Research Period: 2019 Apr. 1 to 2022 Dec. 31

BACKGROUND ART

For neurosurgery through the skull, craniotomy is performed to access the patient brain. In this process, gaps, which are bone defects, occur due to cutting during the surgery. The gap between the bones results in a risk that the brain will be exposed therethrough and hence cannot be safely protected. In addition, the blood flow may be impeded at the incision site, leading to osteolysis. Moreover, the skin is sunken along the gap after the surgery, causing the patient to feel aesthetically unsatisfied.

To solve these problems, conventionally, there has been an approach of filling the gaps with a metal mesh or bone cement.

The procedure using a metal mesh such as titanium (Ti) or titanium alloy has the advantage of preventing some problems such as the sunken skin but has problems such as being unable to promote bone tissue healing and requiring an additional fixing device for fixing the metal mesh to the skull. In addition, when radiation for treatment is performed, since the radiation cannot pass through the metal mesh due to the intrinsic characteristics thereof, the patent cannot receive effective radiation treatment. Moreover, scattering of radiation from the implanted metal may cause side effects such necrosis of surrounding tissues and atrophy of the flap, which may result in the implant being exposed to the outside.

Bone reconstruction for filling skull depressions with a bone cement, which is used as an alternative to the conventional procedure, has partially compensated for the disadvantages of the conventional procedure using the metal mesh. However, the reconstruction technique using a bone cement causes inconvenience to the practitioner due to a long operation time for filling a cranial gap with an arbitrary shape, and there is still a problem that surrounding tissues may be damaged by an exothermic reaction during the cement curing process.

DISCLOSURE

Technical Problem

To effectively solve the problems occurring in the related art, the present invention provides an implant using a biomaterial and a ceramic-based composite material with excellent osteoconductivity in addition to a polymer, in which the implant is a three-dimensional non-fixing implant that can be conveniently used and which is configured to fit in a bone defect. The present invention also provides a method of manufacturing the implant.

In addition, the present invention provides a non-fixing implant manufactured with a 3D printer and a method of manufacturing the same, the implant accurately fitting in a defect created by craniotomy, having improved biocompatibility and bone bonding ability, and allowing tissue penetration.

Technical Solution

A non-fixing implant 10 for craniotomy, according to one embodiment of the present invention, is for reattaching a bone flap 2 removed from the skull 1 during brain surgery. The non-fixing implant 10 includes: a flexible wedge 100 deformable to conform to an external contour of the bone flap 2; and a plurality of wings 200 connected to an upper or lower portion of the flexible wedge 100 and extending from both sides of the flexible wedge 100.

The plurality of wings 200 may have a porous structure, in which each of the wings 200 includes first-side wings 201 to be disposed on the bone flap 2 and second-side wing 202 to be disposed on the skull 1.

The flexible wedge 100 and the plurality of wings 200 are made of a material in which a polymer and a calcium phosphate compound are mixed in a weight ratio in the range of from 10:0 to 5:5 and manufactured through 3D printing using an FDM 3D printer.

Each of the wings 200 has a porous structure having a lattice pattern. The porous structure includes: a first layer in which a plurality of lines extends in a first direction and has a width in the range of from 300 μm to 500 μm and a line spacing in the range of from 300 μm to 500 μm; and a second layer in which a plurality of lines extends in a second direction having an angle of 60° to 120° with the first direction and has a width in the range of from 300 μm to 500 μm and a line spacing in the range of from 300 μm to 500 μm.

In addition, the flexible wedge 100 is composed of a plurality of stacked lines formed on or under the plurality of wings 200. The plurality of stacked lines is composed of protrusions ("∩") and depressions ("∪") that are alternately 15 connected. The plurality of stacked lines is formed such that an A pattern line inclined to have an acute angle with respect to the bottom surface and a B pattern line inclined to have an obtuse angle with respect to the bottom surface are stacked on one another.

In the flexible wedge 100, a width of an upper end thereof is the same as a width of a lower end thereof but is larger than a width of a middle portion thereof. This design enables the skull 1 and the bone flap 2 to be reliably fixed.

The polymer which is one of the materials used for 3D printing of the flexible wedge 100 and the plurality of wings 200 may be one or more selected from the group consisting of polyethylene, metallocene-PE (m-PE), polypropylene, polyisobutylene, poly-4-methylpentene-1, polybutadiene, polyisoprene, polycyclooctene, polystyrene, polymethylstyrene, polyvinylnaphthalene, styrene-butadiene (SB), styrene-butadiene-styrene (SBS), styrene-ethylene-butylene-styrene(SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, polyvinyl chloride (PVC), polychloroprene and polyvinylidene chloride (PVDC), polymethyl methacrylate (PMMA), poly-butyl acrylate, polylauryl acrylate, polystearylacetate, polyacrylonitrile, polyacrylamide, polyamides, polyimides, polyamide imides, polyether imides, polyester imides, poly(ether)ketones, polysulphones, polyethersulphones, polyarylsulphones, polyphenylenesulphide, polybenzimidazoles, polyhydantoins, polyethylene terephthalate (PET), polybutylene terephthalate (PBT), polypropylene (PP) terephtalate, polyethylene naphthylate, poly-1,4-dimethylol cyclohexane terephthalate, polyhydroxybenzoate, polyhydroxynaphthalate, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalate, polyalkylene succinates, poly(malic acid), poly(amino acid), polyvinylpyrrolidone, polyethylene glycol, polyhydroxycellulose, chitin, chitosan, poly(L-lactic acid), poly(lactide-co-glycolide), poly(hydroxybutyrate-co-valerate, copolymers thereof, and terpolymers thereof.

In addition, the calcium phosphate compound may include at least one selected from the group consisting of hydroxyapatite (HAP), carbonated apatite, tricalcium phosphate (TCP), calcium hydrogen phosphate, monocalcium phosphate, dicalcium phosphate, calcium dihydrogen phosphate, tricalcium phosphate, octacalcium phosphate, and calcium pyrophosphate.

The material in which the polymer and the calcium phosphate compound are mixed may further include at least one natural polymeric material selected from the group consisting of carboxyl methyl cellulose, heparan sulfate, hyaluronic acid, collagen, dextran, and alginate.

The material include the polymer and the calcium phosphate compound are mixed or the material in which the polymer, the calcium phosphate compound, and the natural polymeric material are mixed may further include at least one selected from the group consisting of bone morphogenetic proteins (BMP), epidermal growth factors (EGF), fibroblast growth factors (FGF), transforming growth factors (TGFbeta), platelet-derived growth factors (PDGF), vascular endothelial growth factors (VEGE), insulin-like growth factors (IGF-1), thioredoxin (TRX), stem cell factors (SCF), hepatocyte growth factors (HGF), human growth hormones, and angiogenin.

As another embodiment of the present invention, there is provided a method of manufacturing an implant to fill a gap between a skull 1 and a bone flap 2 created by craniotomy, the method including: preparing a composite material by mixing a polymer and a calcium phosphate compound in a weight ratio in a range of from 10:0 to 5:5; printing a plurality of wings 200 using an FDM 3D printer and using the composite material; and forming a flexible wedge 100 by forming a plurality of stacked lines on the plurality of wings 200 using the FDM 3D printer and the composite material.

The plurality of wings 200 may have a porous structure, in which first-side wings 201 of the wings 200 are disposed on the bone flap 2 and second-side wings 202 of the wings 200 are disposed on the skull 1.

The printing of the plurality of wings 200 may include: forming a first layer in which a plurality of lines extends in a first direction and has a width in the range of from 300 μm to 500 μm and a line spacing in the range of from 300 μm to 500 μm; and forming a second layer in which a plurality of lines extends in a second direction having an angle of 60° to 120° with the first direction and has a width in the range of from 300 μm to 500 μm and a line spacing in the range of from 300 μm to 500 μm, in which the forming of the first layer and the forming of the second layer are sequentially performed.

In the forming of the flexible wedge 100, the flexible wedge 100 may be formed to be composed of a plurality of lines stacked on or under the plurality of wings 200, in which the plurality of stacked lines may include protrusions ("∩") and depressions ("∪") that are alternately connected, and the plurality of stacked lines may include an A pattern line inclined to have an acute angle with respect to a bottom surface and a B pattern line inclined to have an obtuse angle.

It is more preferable that the width of the upper end of the flexible wedge 100 be the same as the width of the lower end of the flexible wedge 100 and be larger than the width of a middle portion of the flexible wedge 100.

Advantageous Effects

The non-fixing implant for craniotomy, according to the present invention, is made of a material including a polymer such as polycaprolactone (PCL) or the like so as to have high elongation. Therefore, the non-fixing implant can be flexibly applied even to curved defects that are generated by craniotomy, due to the high elongation thereof. In addition, since the non-fixing implant has a wedge-shaped insert to be inserted into a skull defect, the non-fixing implant can be fixed without using an additional fixing device after being inserted. This means that the non-fixing implant has the ability to accurately bind to the defect.

In addition, the material of the non-fixing implant according to the present invention may further include a ceramic compound such as calcium phosphate. Therefore, the material of the non-fixing implant is crystallographically and chemically similar to inorganic components constituting actual bone and has the ability to directly bind to the bone and excellent osteoconductivity.

In addition, when a biodegradable substance or a biodegradable polymer is used for the non-fixing implant, the non-fixing implant has a decomposition period of about 24 months due to the characteristic of being absorbed in the body, and thus a separate removal process is not required. In addition, due to the unique porous structure, tissues can penetrate into the implant, and the implant can be replaced by new bone or absorbed into the body.

EXPLANATION OF REFERENCE NUMERALS IN THE DRAWINGS

Figure 1:
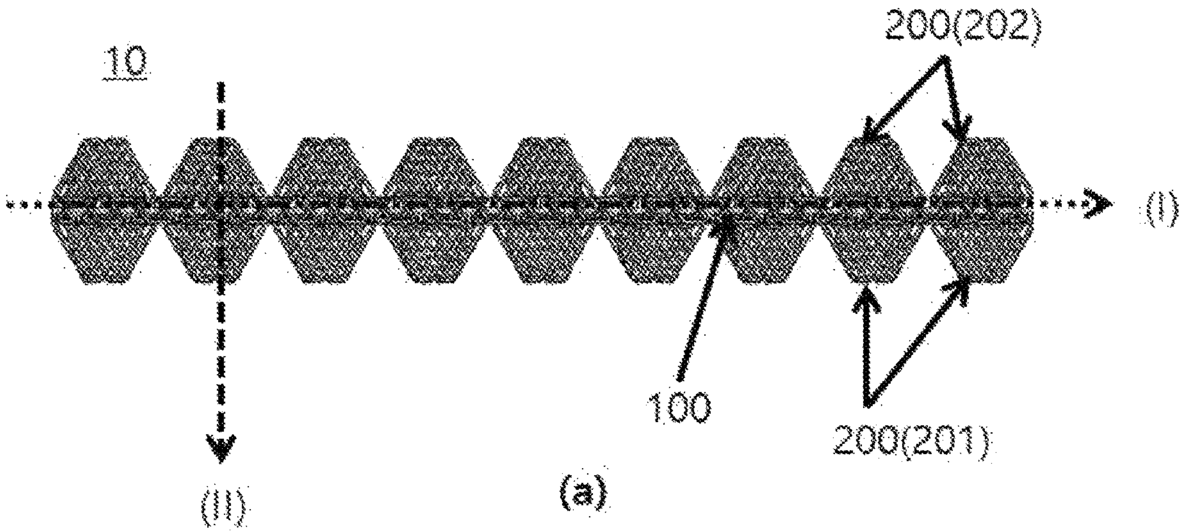
In FIG. 1, (*a*) and (*b*) are respectively a plan view and a perspective view of a non-fixing implant for craniotomy, according to the present invention.
Figure 1:
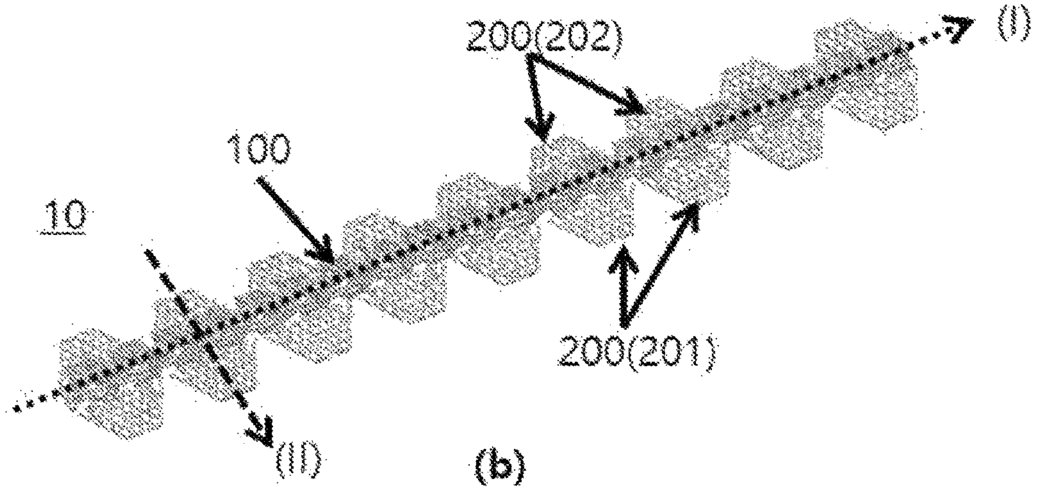

1: Skull
2: Bone flap
10: Non-fixed implants for craniotomy
100: Flexible wedge
200: Wing portion
201: First wing
202: Second wing

BEST MODE

Prior to describing preferred embodiments of the present disclosure, it should be noted that the terms and words used in the present specification and the appended claims should not be construed as being limited to conventional or dictionary meanings but should be construed as meaning and concept consistent with the technical idea of the present invention.

It will be further understood that the terms "comprises" and/or "comprising", or "includes" and/or "including", or "has" and/or "having", when used in this specification, specify the presence of stated features, regions, integers, steps, operations, elements, and/or components, but do not preclude the presence or addition of one or more other features, regions, integers, steps, operations, elements, and/or components.

Herein after, embodiments of the present disclosure will be described. However, the scope of the present disclosure is not limited to the preferred embodiments described below, and those skilled in the art may implement various modified forms of the contents described herein without departing from the scope of the present disclosure.

A non-fixing implant for craniotomy, according to the present invention, is constructed in a manner to accurately fix a defect created by craniotomy. The non-fixing implant has improved biocompatibility and bone bonding ability and allows tissue penetration. The non-fixing implant is manufactured with a FDM 3D printer.

Figure 2:
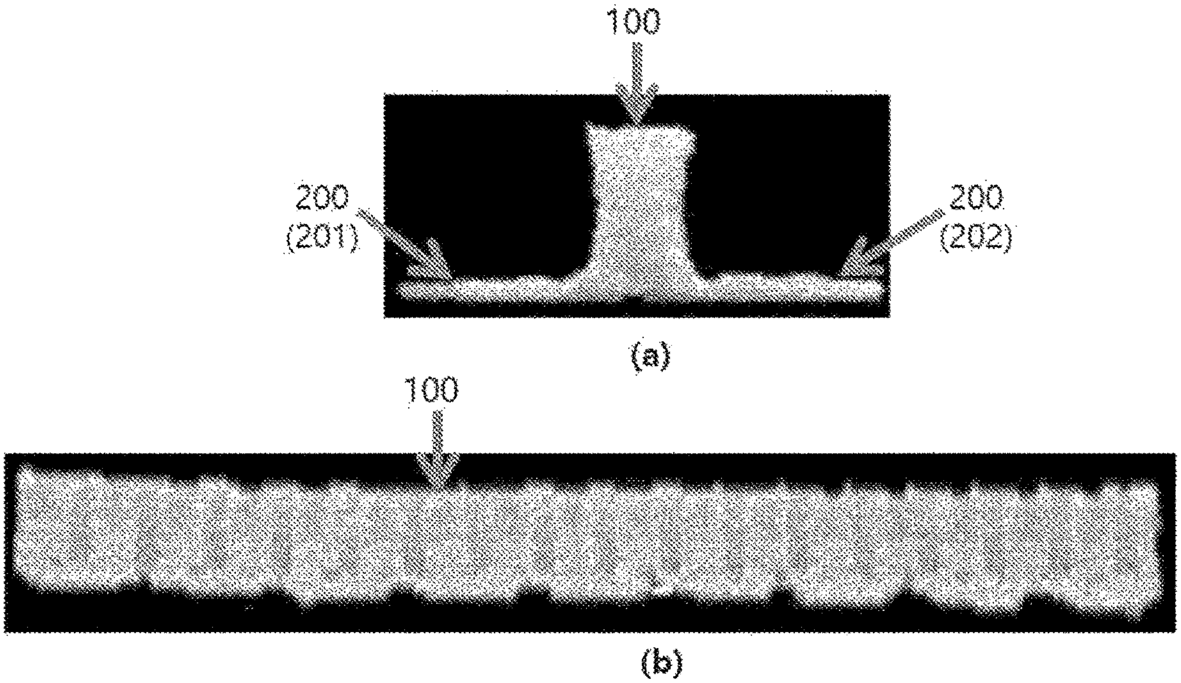
In FIG. 2, (*a*) and (*b*) are cross-sectional views taken in I and II directions of FIG. 1, respectively.

Referring to FIGS. 1 and 2, a non-fixing implant 10 for craniotomy, according to one embodiment of the present invention, is used to reattach a bone flap 2 removed from the skull 1 during brain surgery. The non-fixing implant 10 includes: a flexible wedge 100 deformable conforming to an external contour of the bone flap 2; and a plurality of wings 200 connected to an upper or lower portion of the flexible wedge 100 and extending toward both sides of the flexible wedge 100.

The plurality of wings 200 may have a porous structure, in which first-side wings 201 (or 202) of the wings 200 are disposed on the bone flap 2 and second-side wings 202 (or 201) of the wings 200 are disposed on the skull 1.

The flexible wedge 100 and the plurality of wings 200 are made of a mixed material in which a polymer and a calcium phosphate compound are mixed in a weight ratio in the range of from 10:0 to 5:5 and are manufactured through 3D printing using an FDM 3D printer.

As the calcium phosphate compound, it is preferable to use β-tricalcium phosphate (β-TCP). The β-tricalcium phosphate (β-TCP) is pulverized with a mortar and sieved to have an average particle size of about 100 μm.

First, as illustrated in the plan view (a) and the perspective view (b) of FIG. 1, the wing 200 has a multi-layered structure in which a plurality of lines is arranged at regular intervals in each layer. That is, the wing 200 includes: a first layer in which a plurality of lines extends in a first direction and has a width in the range of from 300 μm to 500 μm and a line spacing in the range of from 300 μm to 500 μm; and a second layer in which a plurality of lines extends in a second direction having an angle of 60° to 120° with the first direction and has a width in the range of from 300 μm to 500 μm and a line spacing in the range of from 300 μm to 500 μm.

The wing 200 is configured in such a manner that the basic unit composed of the first layer and the second layer sequentially stacked is repeatedly stacked one to five times.

The line width and the line spacing may be the same for each layer. Alternatively, the line with and the line spacing may vary within appropriate ranges for each layer. When the constituent lines have predetermined widths and spacings so as to be directionally arranged, the wings have not only good mechanical strength but also sufficient elasticity and flexibility.

As illustrated in FIG. 1, the wings 200 preferably have a polygonal shape such as a hexagonal shape, and thus the width of each wing 200 is longest at the center thereof where the wedge 100 is perpendicularly formed on top thereof. In addition, in the wings 200, the left side of the center portion and the right side of the center portion are preferably symmetrical. Although each of the wings 200 preferably has a hexagonal shape, the shape of the wings 200 is not limited thereto.

The wedge 100 is vertically formed on top of the center portion of the wing 200 by an FDM 3D printing process. Preferably, the wedge 100 is made of the same material as the wing 200. The wedge 100 formed to protrude from the top of the wing 200 is line-shaped and has an inclination angle in the range of from 60° to 120° with respect to a horizontal direction (0°). The line spacing of the wedge 100 may be in the range of from 2 mm to 3 mm (P in FIG. 3), and the line spacing is uniform and continuous as if the line spacing is drawn in a single line drawing manner (see FIG. 3).

Figure 3:
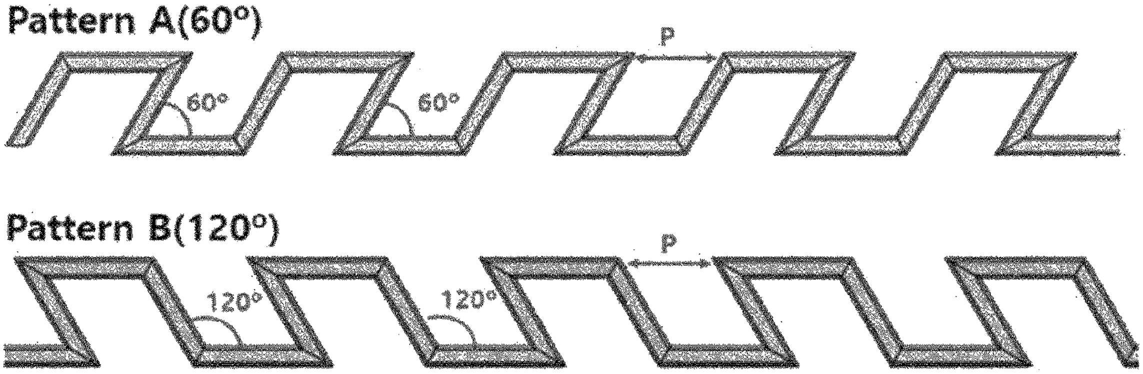
FIG. 3 is a schematic view illustrating an exemplary pattern of a wedge of the non-fixing implant for craniotomy, according to the present invention, in which A patterns and B patterns are alternately arranged.

In this case, the height of one layer of the wedge 100 is in the range of from 100 μm to 200 μm, and the total height of the wedge 100 is preferably in the range of from 3 mm to 8 mm. At the time of forming each layer of the wedge 100, the transverse flexibility can be adjusted by controlling the spacing between the lines (P in FIG. 3). In this case, it is preferable that the A pattern and the B pattern are alternatively provided in the layers as illustrated in FIG. 3. This arrangement can prevent the implant from being bendable only in one direction or prevent the implant from having unidirectional flexibility.

When the A pattern and the B pattern are alternately stacked, the A pattern and the B pattern layer may be alternate for every layer (for example, A-B-A-B-A-B- . . . ) as illustrated in FIG. 3.

Alternatively, the A pattern and the B pattern may be alternate for every two layers (for example, A-A-B-B-A-A-B-B- . . . ) or for every three layers (for example, A-A-A-B-B-B- . . . ) as shown in Tables 1 to 3. In this case, a total of six or more layers may be stacked according to the stacking rules. The number of the staked layers is not necessarily limited to 6 as shown in Tables 1 to 3.

That is, the flexible wedge 100 is composed of a plurality of lines stacked on or under the center portion of the plurality of wings 200. Each of the plurality of lines has a pattern in which protrusions ("∩") and depressions ("∪") are alternately connected. Each of the plurality of lines has the A pattern inclined to have an acute angle with respect to the bottom surface or the B pattern inclined to have an obtuse angle with respect to the bottom surface. When the inclination angle of the A pattern is in the range of from 45° to 90°, and the inclination angle of the B pattern is in the range of from 135° to 90°, the sum of the inclination angle of the A pattern and the inclination angle of the B pattern is preferably equal to 180° so that the A pattern and the B pattern are complementary to each other.

TABLE 1

| Layer No. | | Alternating patterns for each layer (A-B-A-B-A-B) |
|---|---|---|
| 1 | 60° | 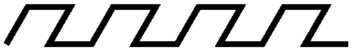 |
| 2 | 120° | 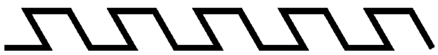 |
| 3 | 60° | 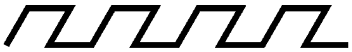 |
| 4 | 120° | 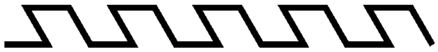 |
| 5 | 60° | 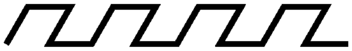 |
| 6 | 120° | 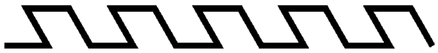 |

TABLE 2

| Layer No. | | Alternating patterns every two layers (A-A-B-B-A-A) |
|---|---|---|
| 1 | 60° | 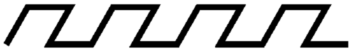 |
| 2 | 60° | 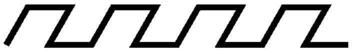 |
| 3 | 120° | 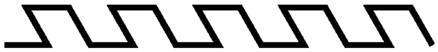 |

TABLE 2-continued

| Layer No. | | Alternating patterns every two layers (A-A-B-B-A-A) |
|---|---|---|
| 4 | 120° | 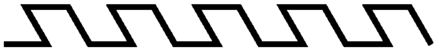 |
| 5 | 60° | 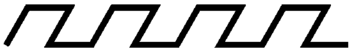 |
| 6 | 60° | 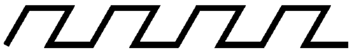 |

TABLE 3

| Layer No. | | Alternating patterns every three layers (A-A-A-B-B-B) |
|---|---|---|
| 1 | 60° | 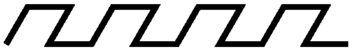 |
| 2 | 60° | 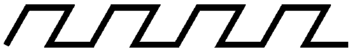 |
| 3 | 60° | 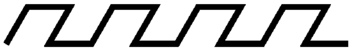 |
| 4 | 120° | 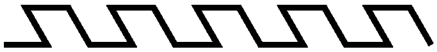 |
| 5 | 120° | 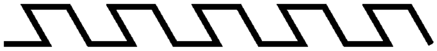 |
| 6 | 120° | 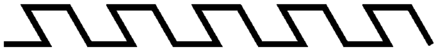 |

The vertical cross section taken by cutting along the longitudinal direction (direction I of FIG. 1) of the wedge 100 protruding on the center portion of the wing 200 is illustrated in (b) of FIG. 2, and the vertical cross section taken by cutting along the direction (i.e., direction II of FIG. 1) of the longest width of the wing 200, including the width of the wedge 100, is illustrated in (a) of FIG. 2.

As illustrated in (a) of FIG. 2, preferably, the width of the upper end of the flexible wedge 100 is equal to the width of the lower end of the flexible wedge 100 and is larger than the width of a middle portion of the wedge 100.

The wedge 100 is inserted into the gap between the bone flap 2 and the skull 1 during craniotomy. Therefore, in the case where the widths at the upper and lower ends are larger than the width of the middle portion, the wedge can be stably fixed once the wedge 100 is inserted.

Figure 4:
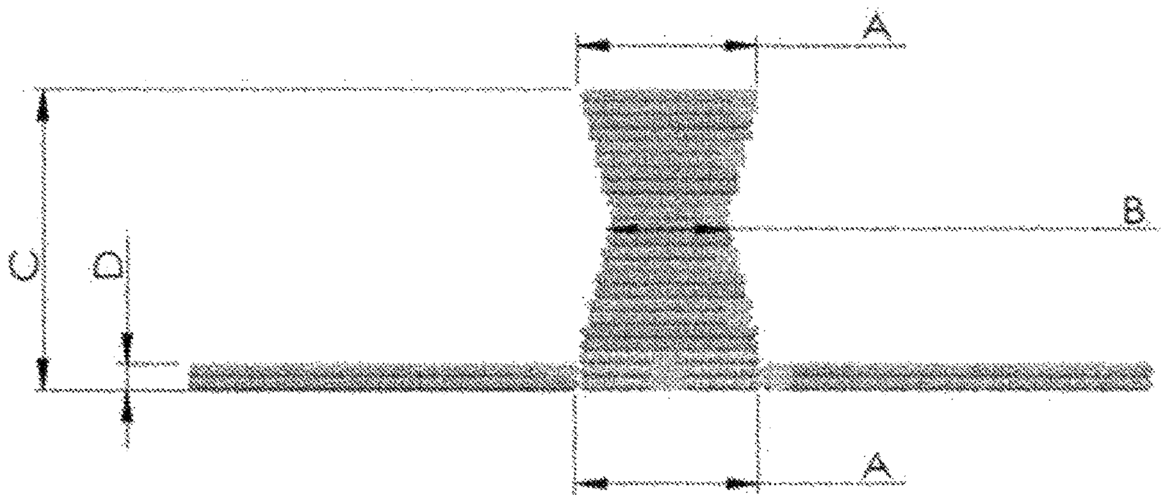
FIG. 4 is a schematic view illustrating a cross-sectional structure of the wedge of the non-fixing implant for craniotomy, according to the present invention.

FIG. 4 schematically illustrates cross-sectional structures of the wedge and wing of the craniotomy non-fixing implant 10 having the shape illustrated in (a) of FIG. 2, according to the present invention. As described above, the width of the first layer of the wedge and the width of the last layer of the wedge are the same (see FIG. 4, A), and the width is preferably in the range of from 3 mm to 10 mm. In addition, a middle portion of the wedge (see FIG. 4, B) is relatively narrow, and the width of the middle portion is preferably in the range of from 2 mm to 9 mm.

The craniotomy non-fixing implant with this structure is made of a composite material in which a polymer and a calcium phosphate compound are mixed in a weight ratio in the range of from 10:0 to 5:5.

The polymer used in the invention includes one or more selected from the group consisting of polyethylene, metallocene-PE (m-PE), polypropylene, polyisobutylene, poly-4-methylpentene-1, polybutadiene, polyisoprene, polycyclooctene, polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, polyvinyl chloride (PVC), polychloroprene and polyvinylidene chloride (PVDC), polymethyl methacrylate (PMMA), poly-butyl acrylate, polylauryl acrylate, polystearylacetate, polyacrylonitrile, polyacrylamide, polyamides, polyimides, polyamide imides, polyether imides, polyester imides, poly(ether) ketones, polysulphones, polyethersulphones, polyarylsulphones, polyphenylenesulphide, polybenzimidazoles, polyhydantoins, polyethylene terephthalate (PET), polybutylene terephthalate (PBT), polypropylene (PP) terephtalate, polyethylene naphthylate, poly-1,4-dimethylol cyclohexane terephthalate, polyhydroxybenzoate, polyhydroxynaphthalate, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalate, polyalkylene succinates, poly(malic acid), poly(amino acid), polyvinylpyrrolidone, polyethylene glycol, polyhydroxycellulose, chitin, chitosan, poly(L-lactic acid), poly(lactide-co-glycolide), poly(hydroxybutyrate-co-valerate, copolymers thereof, and terpolymers thereof. However, the polymer that can be used in the invention is not limited thereto.

In addition, the calcium phosphate compound is an inorganic component similar to that of natural bone. As the calcium phosphate compound, any calcium phosphate can be used without particular limitation if it can help the bone to grow through conduction.

For example, at least one selected from the group consisting of hydroxyapatite (HAP), carbonated apatite, tricalcium phosphate (TCP), calcium hydrogen phosphate, monocalcium phosphate, dicalcium phosphate, calcium dihydrogen phosphate, tricalcium phosphate, octacalcium phosphate, and calcium pyrophosphate may be used.

Optionally, in addition to the polymer and the calcium phosphate compound, at least one more natural polymeric material such as carboxyl methyl cellulose, heparan sulfate, hyaluronic acid, collagen, dextran, or alginate may be further included. Preferably, the natural polymeric material may be included in an amount of 100 parts by weight or less per 100 parts by weight of the polymer.

Optionally, in addition to the polymer and the calcium phosphate compound, at least one selected from the following may be further included preferably in an amount of 1.0 parts by weight or less per 100 parts by weight of the polymer: bone morphogenetic proteins (bmp), epithelial cell growth factors (EGF), fibroblast growth factors (FGF), conversion growth factors (TGFbeta), platelet-derived growth factors (PDGF), vascular endothelial growth factors (veg), insulin-like growth factors (IGF-1), thioredoxin (TRX), stem cell factors (SCF), hepatocyte proliferation factors (HGF), human growth hormones, and angiogenin.

Figure 5:
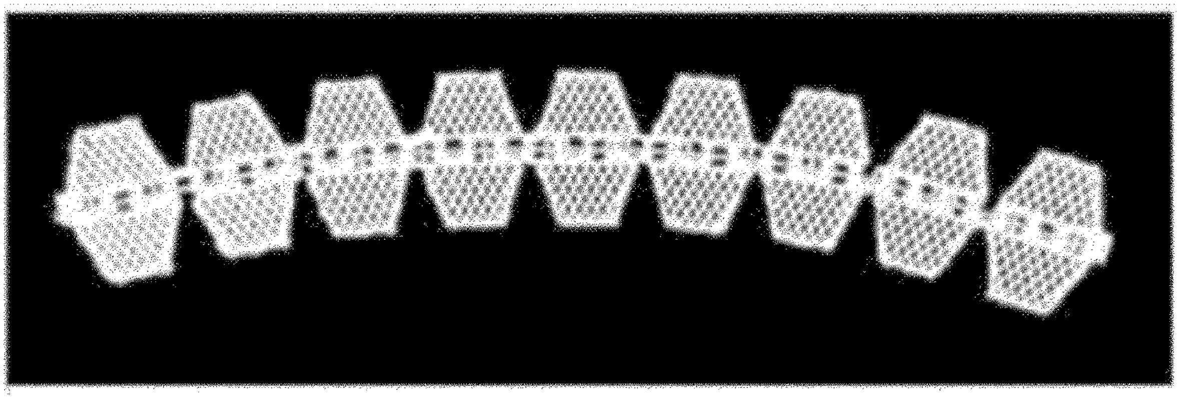
FIG. 5 is a picture illustrating the flexibility of the non-fixing implant for craniotomy, according to the present invention.
Figure 5:
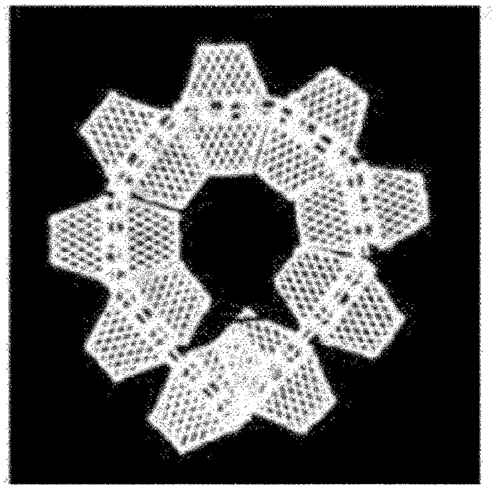

FIG. 5 illustrates pictures of the non-fixing implant 10 for craniotomy according to one embodiment of the present invention when a physical force is applied to bend the implant in various ways, to investigate the constitutional components of the implant and to examine the flexibility which is a structural characteristic of the wing and wedge of the implant.

When a physical force was applied, it was confirmed that the implant was flexibly bent without breaking. The confirmation indicates that even though craniotomy incisions with various curvatures are made, the implant can be fixed to the skull 1 and the bone flap 2 while filling the gap between the skull 1 and the bone flap 2 (in which the wing may be provided with a hole to receive a screw for fixing the implant to the skull and the bone flap).

In the case of an existing implant, the center portion corresponding to the wedge of the implant of the present invention has a straight bar-like structure. Therefore, the bendable angle of the existing implant is limited when the implant has a sufficient mechanical strength (that is, when the mechanical strength is satisfactory, the bendable angle is not sufficient). In the case of the implant of the present invention, as can be seen from FIG. 1 and Tables 1 to 3, both the mechanical strength and the flexibility can be maximized due to the wedge-shaped center portion which is the feature of the present invention. For example, as illustrated in (b) of FIG. 5, the implant of the present invention can be bent by 360°.

As another embodiment of the present invention, there is provided a method of manufacturing a non-fixing implant 10 for craniotomy. The method includes: preparing a composite material by mixing a polymer and a calcium phosphate compound in a weight ratio in the range of from 10:0 to 5:5; printing a plurality of wings 200 using an FDM 3D printer and the prepared composite material; and forming a flexible wedge 100 on the plurality of wings 200 by stacking a plurality of lines using the FDM 3D printer and the composite material.

The plurality of wings 200 has a porous structure. The wings 201 on one side are disposed on the bone flap 2, and the wings 202 on the opposite side are disposed on the skull 1. The wings 201 and 202 may be provided with holes to receive screws for fixing the non-fixing implant to the skull and the bone flap during craniotomy.

In order to produce the implant of the invention by 3D printing using an FDM 3D printer and the composite material in which the polymer and the calcium phosphate compound are mixed, the polymer was first introduced into a mixing container and then melted at 160° C.±20° C. for 40 minutes, and the calcium phosphate is then weighed and mixed with the molten polymer. For uniform blending, the mixture was stirred at a speed of about 1200 rpm for 2 minutes. The 20-minute stirring was repeated a total of about six times.

The composite material produced in this manner was placed in a cylinder of a 3D printer and was ejected through a 500-μm nozzle. In this case, the ejection temperature was maintained at 120° C. and the pneumatic pressure for ejection was maintained at 500 kPa. The printing speed was varied for each layer, but the printing speed for every layer was controlled to fall within the range of from 700 mm/min to 1000 mm/min.

Figure 6:
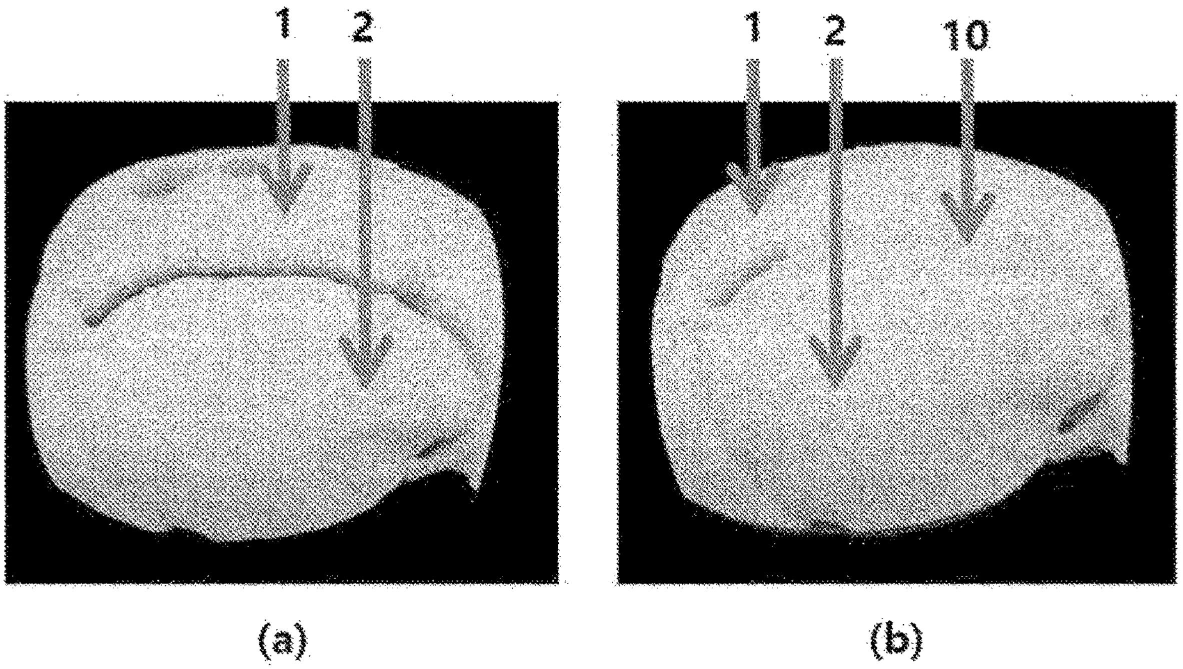
FIG. 6 is a picture illustrating states before and after reattachment of the bone flap 2 to the skull 1 by using the non-fixing implant for craniotomy, according to the present invention.

The pictures of the non-fixing implant 10 produced in the manner described above are shown in FIG. 6. In FIG. 6, (*a*) is a picture taken before the implantation and (*b*) is a picture taken after the implantation. It is seen that the non-fixing implant 10 for craniotomy, according to the present invention, is disposed between the skull 1 and the flap 2 to fix the skull 1 and the flap 2.

The present disclosure is not limited to the above-described specific embodiments and description, and various changes and modifications thereof may be made without departing from the scope of the present disclosure as defined in the appended claims by those skilled in the art. In addition, such variations may fall within the protection scope of the present disclosure.

INDUSTRIAL APPLICABILITY

The present invention is intended to provide an implant by using a ceramic composite material and a biomaterial having good osteoconductivity along with a polymer. Specifically, the present invention provides a non-fixing implant that is three-dimensionally designed so as to be accurately inserted into a gap and which can be conveniently used. The implant is a 3D-printed implant that can be accurately bound to a defect created by craniotomy, has improved biocompatibility and bone bonding ability, and allows tissue invasion. In addition, the present invention provides a method of manufacturing such an implant.

The non-fixing implant for craniotomy, according to the present invention, is made of a material including a polymer such as polycaprolactone (PCL) or the like so as to have high elongation. Therefore, the non-fixing implant can be flexibly applied even to curved defects that are generated by craniotomy, due to the high elongation thereof. In addition, since the non-fixing implant has a wedge-shaped insert to be inserted into a skull defect, the non-fixing implant can be fixed without using an additional fixing device after being inserted. This means that the non-fixing implant has the ability to accurately bind to the defect and hence have industrial applicability.

The invention claimed is:

1. A non-fixing implant for filling a gap between a skull (1) and a bone flap (2) created by craniotomy, the implant comprising:

- a flexible wedge (100) deformable to conform to an external contour of the bone flap (2); and
- a plurality of wings (200) connected to an upper or lower portion of the flexible wedge (100) and extending to both sides of the flexible wedge (100),
- wherein the plurality of wings (200) has a porous structure, wherein first-side wings (201) of the plurality of wings (200) are to be disposed on the bone flap (2) and second-side wings (202) of the plurality of wings are to be disposed on the skull (1),
- the flexible wedge (100) comprises a plurality of stacked lines disposed on or under the plurality of wings (200),
- the plurality of stacked lines has a structure in which protrusions and depressions are alternately connected, including a first pattern line inclined to have an acute angle with a bottom surface and a second pattern line inclined to have an obtuse angle with the bottom surface.

2. The implant of claim 1, wherein the flexible wedge (100) and the plurality of wings (200) are made of a mixed material in which a polymer and a calcium phosphate compound are mixed in a weight ratio in a range of from 10:0 to 5:5 and are manufactured through 3D printing using an FDM 3D printer.

3. The implant of claim 2, wherein the polymer comprises one or more selected from the group consisting of polyethylene, metallocene-PE (m-PE), polypropylene, polyisobutylene, poly-4-methylpentene-1, polybutadiene, polyisoprene, polycyclooctene, polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene -styrene, styrene-isoprene, styrene-isoprene-styrene (SIS), styrene-butadiene-acrylonitrile (ABS), styrene-acrylonitrile-acrylate (ASA), styrene-ethylene, polyvinyl chloride (PVC), polychloroprene and polyvinylidene chloride (PVDC), polymethyl methacrylate (PMMA), poly-butyl acrylate, polylauryl acrylate, polystearylacetate, polyacrylonitrile, polyacrylamide, polyamides, polyimides, polyamide imides, polyether imides, polyester imides, poly(ether)ketones, polysulphones, polyethersulphones, polyarylsulphones, polyphenylenesulphide, polybenzimidazoles, polyhydantoins, polyethylene terephthalate (PET), polybutylene terephthalate (PBT), polypropylene (PP) terephtalate, polyethylene naphthylate, poly-1,4-dimethylol cyclohexane terephthalate, polyhydroxybenzoate, polyhydroxynaphthalate, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalate, polyalkylene succinates, poly (malic acid), poly (amino acid), polyvinylpyrrolidone, polyethylene glycol, polyhydroxycellulose, chitin, chitosan, poly (L-lactic acid), poly (lactide-co-glycolide), poly (hydroxybutyrate-co-valerate, copolymers thereof, and terpolymers thereof.

4. The implant of claim 2, wherein the calcium phosphate compound comprises at least one selected from the group consisting of hydroxyapatite (HAP), carbonated apatite, tricalcium phosphate (TCP), calcium hydrogen phosphate, monocalcium phosphate, dicalcium dihydrogen phosphate, tricalcium phosphate, octacalcium phosphate, and calcium pyrophosphate.

5. The implant of claim 2, wherein the mixed material in which the polymer and the calcium phosphate compound are mixed further comprises at least one natural polymeric material selected from the group consisting of carboxyl methyl cellulose, heparan sulfate, hyaluronic acid, collagen, dextran, and alginate.

6. The implant of claim 2, wherein the mixed material in which the polymer and the calcium phosphate compound are mixed further comprises at least one selected from the group consisting of bone morphogenetic proteins (BMP), epidermal growth factors (EGF), fibroblast growth factors (FGF), transforming growth factors (TGFbeta), platelet-derived growth factors (PDGF), vascular endothelial growth factors (VEGE), insulin-like growth factors (IGF-1), thioredoxin (TRX), stem cell factors (SCF), hepatocyte growth factors (HGF), human growth hormones, and angiogenin.

7. The implant of claim 1, wherein the wing (200) has a porous structure with a lattice pattern, the wing comprising:

- a first layer in which a plurality of lines extends in a first direction and has a width in a range of from 300 μm to 500 μm and a ling spacing in a range of from 300 μm to 500 μm; and
- a second layer in which a plurality of lines extends in a second direction having an angle in a range of from 60° to 120° with respect to the first direction and has a width in a range of from 300 μm to 500 μm and a line spacing in a range of from 300 μm to 500 μm.

8. The implant of claim 1, wherein in the flexible wedge (100), a width of an upper end thereof is equal to a width of a lower end thereof but is larger than a width of a middle portion thereof.

9. A method of manufacturing a non-fixing implant (10) for filling a gap between a skull (1) and a bone flap (2) caused by craniotomy, the method comprising:

preparing a material by mixing a polymer and a calcium phosphate compound in a weight ratio in a range of from 10:0 to 5:5;

printing a plurality of wings (200) using an FDM 3D printer and the material; and forming a flexible wedge (100) by stacking a plurality of lines using the FDM 3D printer and the material on the plurality of wings (200), wherein the plurality of wings (200) has a porous structure, wherein first-side wings (201) of the plurality of wings (200) are to be disposed on the bone flap (2) and second-side wings (202) of the plurality of wings are to be disposed on the skull (1), the forming of the flexible wedge (100) is performed such that the flexible wedge (100) comprises a plurality of stacked lines disposed on or under the plurality of wings (200), the plurality of stacked lines has a structure in which protrusions and depressions are alternately connected, including a first pattern line inclined to have an acute angle with a bottom surface and a second pattern line inclined to have an obtuse angle with the bottom surface.

10. The method of claim 9, the printing of the plurality of wings (200) comprises:

forming a first layer in which a plurality of lines extends in a first direction and has a width in a range of from 300 μm to 500 μm and a ling spacing in a range of from 300 μm to 500 μm; and forming a second layer in which a plurality of lines extends in a second direction having an angle in a range of from 60° to 120° with respect to the first direction and has a width in a range of from 300 μm to 500 μm and a line spacing in a range of from 300 μm to 500 μm, wherein the forming of the first layer and the forming of the second layer are sequentially performed at least two times.

11. The method of claim 9, wherein in the flexible wedge (100), a width of an upper end thereof is equal to a width of a lower end thereof but is larger than a width of a middle portion thereof.

12. The method of claim 9, wherein the polymer comprises one or more selected from the group consisting of polyethylene, metallocene-PE (m-PE), polypropylene, polyisobutylene, poly-4-methylpentene-1, polybutadiene, polyisoprene, polycyclooctene, polystyrene, polymethylstyrene, polyvinylnaphthalene, styrene-butadiene (SB), styrene-butadiene-styrene (SBS), styrene-ethylene-butylene-styrene (SEBS), styrene-ethylene-propylene -styrene, styrene-isoprene, styrene-isoprene-styrene (SIS), styrene-butadiene-acrylonitrile (ABS), styrene-acrylonitrile-acrylate (ASA), styrene-ethylene, polyvinyl chloride (PVC), polychloroprene and polyvinylidene chloride (PVDC), polymethyl methacrylate (PMMA), poly-butyl acrylate, polylauryl acrylate, polystearylacetate, polyacrylonitrile, polyacrylamide, polyamides, polyimides, polyamide imides, polyether imides, polyester imides, poly(ether)ketones, polysulphones, polyethersulphones, polyarylsulphones, polyphenylenesulphide, polybenzimidazoles, polyhydantoins, polyethylene terephthalate (PET), polybutylene terephthalate (PBT), polypropylene (PP) terephtalate, polyethylene naphthylate, poly-1,4-dimethylol cyclohexane terephthalate, polyhydroxybenzoate, polyhydroxynaphthalate, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalate, polyalkylene succinates, poly(malic acid), poly(amino acid), polyvinylpyrrolidone, polyethylene glycol, polyhydroxycellulose, chitin, chitosan, poly(L-lactic acid), poly(lactide-co-glycolide), poly(hydroxybutyrate-co-valerate, copolymers thereof, and terpolymers thereof.

13. The method of claim 9, wherein the calcium phosphate compound comprises at least one selected from the group consisting of hydroxyapatite (HAP), carbonated apatite, tricalcium phosphate (TCP), calcium hydrogen phosphate, monocalcium phosphate, dicalcium dihydrogen phosphate, tricalcium phosphate, octacalcium phosphate, and calcium pyrophosphate.

14. The method of claim 9, wherein the mixed material in which the polymer and the calcium phosphate compound are mixed further comprises at least one natural polymeric material selected from the group consisting of carboxyl methyl cellulose, heparan sulfate, hyaluronic acid, collagen, dextran, and alginate.

15. The method of claim 9, wherein the mixed material in which the polymer and the calcium phosphate compound are mixed further comprises at least one selected from the group consisting of bone morphogenetic proteins (BMP), epidermal growth factors (EGF), fibroblast growth factors (FGF), transforming growth factors (TGFbeta), platelet-derived growth factors (PDGF), vascular endothelial growth factors (VEGE), insulin-like growth factors (IGF-1), thioredoxin (TRX), stem cell factors (SCF), hepatocyte growth factors (HGF), human growth hormones, and angiogenin.

* * * * *